United States Patent [19]

Hanada et al.

[11] Patent Number: 4,468,386

[45] Date of Patent: Aug. 28, 1984

[54] 1-DEAMINO-1-HYDROXY-AMINOGLYCO-SIDE COMPOUNDS, ANTIBACTERIAL COMPOSITIONS AND METHOD OF USE

[75] Inventors: Minoru Hanada, Tokyo; Mitsuaki Tsunakawa, both of Tokyo; Koji Tomita, Kawasaki; Hiroshi Tsukiura, Sendai; Hiroshi Kawaguchi, Tokyo, all of

[73] Assignee: Bristol-Myers Company, New York, N.Y.

[21] Appl. No.: 409,740

[22] Filed: Aug. 19, 1982

[51] Int. Cl.³ .................... A61K 31/71; C12P 19/50; C12P 19/52; C07H 15/22
[52] U.S. Cl. .................... 424/181; 435/82; 435/83; 536/13.2; 536/13.3; 536/16.6; 536/16.8
[58] Field of Search ............. 424/181; 536/13.2, 13.3, 536/16.8, 16.6

[56] References Cited

U.S. PATENT DOCUMENTS 4,065,615  12/1977  Horii et al. .................... 536/13.2

OTHER PUBLICATIONS

Nakayama et al., "Chem. Abst." vol. 92, p. 92700(d), 1980
"Chem. Abst." vol. 94, p. 119467(p)
Fujiwara et al., "The Jour. of Antibiotics", vol. XXXIII, No. 8, pp. 836–841, 1980.
Shirahata et al., "The Jour. of Antibiotics", vol. XXXV, No. 4, pp. 520–523, 1982

*Primary Examiner*—Johnnie R. Brown
*Attorney, Agent, or Firm*—Richard R. Lloyd

[57] ABSTRACT

Antibiotic Bu-2659 complex, containing components A, B, C, D and E, is produced by cultivation of *Streptomyces hygroscopicus* Strain No. J296-21, ATCC No. 39150.

8 Claims, 6 Drawing Figures

FIG. 1
INFRARED ABSORPTION SPECTRUM OF Bu-2659A

FIG. 2
PMR SPECTRUM OF Bu-2659A

FIG. 3 PMR SPECTRUM OF Bu-2659B

FIG. 4
PMR SPECTRUM OF Bu-2659C

FIG. 5
PMR SPECTRUM OF Bu-2659D

FIG. 6
PMR SPECTRUM OF Bu-2659E

1-DEAMINO-1-HYDROXY-AMINOGLYCOSIDE COMPOUNDS, ANTIBACTERIAL COMPOSITIONS AND METHOD OF USE

SUMMARY OF THE INVENTION

This invention relates to novel antibiotic substances. More particularly, it relates to an antibiotic complex designated as Bu-2659, said complex being produced by cultivating a strain of *Streptomyces hygroscopicus* having the identifying characteristics of ATCC No. 39150 under submerged aerobic conditions in an aqueous nutrient medium until a substantial amount of Bu-2659 is produced in the culture medium and, optionally, recovering Bu-2659 from the culture medium.

This invention also provides five novel antibiotic components of Bu-2659, designated Bu-2659A, Bu-2659B, Bu-2659C, Bu-2659D and Bu-2659E, which are recovered from Bu-2659 complex by chromatographic procedures.

The Bu-2659 components A-E are structurally related to the neomycin, paromomycin and ribostamycin groups of antibiotics, but differ in that the aglycone of the Bu-2659 components is 1-deamino-1-hydroxy-2-deoxystreptamine.

DESCRIPTION OF THE PRIOR ART

There have been several recent examples of the production of aminoglycoside antibiotics containing the 1-deamino-1-hydroxy-2-deoxystreptamine moiety as the aglycone. Each of these were produced by fermentation of a 2-deoxystreptamine-negative mutant of a known microorganism. The preparation of Bu-2659 is the first instance of a 1-deamino-1-hydroxy-2-deoxystreptamine-containing aminoglycoside being produced by fermentation of a naturally occurring microorganism.

Published Japan Patent Application (Kokai) No. 54-117,477 [Chem. Abst. 92, 92700d (1980)] discloses antibiotic SUM-3, which is the 1-deamino-1-hydroxy analog of sagamicin. SUM-3 was produced by fermentation of *Micromonospora sagamiensis* SU-2 (FERM-P 4230, NRRL 11182) which is a 2-deoxystreptamine-negative mutant of the sagamicin-producing microorganism.

Published Japan Patent Application (Kokai) No. 55-99,196 [Chem. Abst. 94, 119467p (1981)] discloses antibiotics K-144e and K-144g, which are the 1-deamino-1-hydroxy analogs of gentamicin $X_2$ and G418, respectively. They also were produced by fermentation of *Micromonospora sagamiensis* SU-2.

The Journal of Antibiotics, 33, 836-841 (1980) discloses antibiotic S-11-A, which is the 1-deamino-1-hydroxy analog of xylostasin. It was produced by fermentation of *Bacillus circulans* S-11 (FERM-P 5220), a 2-deoxystreptamine-negative mutant of the xylostasin-producing microorganism *Bacillus circulans* Mot 3. The structures of Bu-2659E and S-11-A are closely related, the difference being in the pentose moiety. Bu-2659E contains ribose while S-11-A contains xylose.

The Journal of Antibiotics, 35, 520-523 (1982) discloses antibiotics SU-1, SU-2, and SU-3, which are the 1-deamino-1-hydroxy analogs of gentamicin $C_2$, gentamicin $C_{1a}$ and sagamicin, respectively. They are prepared by fermentation of a 2-deoxystreptamine idiotrophic mutant of the sagamicin producer *Micromonospora sagamiensis* KY-11509.

COMPLETE DESCRIPTION

Bu-2659 complex and its components Bu-2659A, B, C, D and E may be produced by fermentation of *Streptomyces hygroscopicus* strain J296-21 (ATCC No. 39150). The structures of Bu-2659A, B, C, D and E (along with that of a bioactive degradation product of Bu-2659A designated as Bu-2659 DP-I) are as shown in Structures I and II below. The structures of neomycins B and C, paromomycins I and II, ribostamycin and neamine are also shown for comparison purposes.

|  | $R_1$ | $R_2$ | $R_3$ | $R_4$ |
|---|---|---|---|---|
| Bu-2659A | $NH_2$ | OH | H | $CH_2NH_2$ |
| Bu-2659B | $NH_2$ | OH | $CH_2NH_2$ | H |
| Bu-2659C | OH | OH | H | $CH_2NH_2$ |
| Bu-2659D | $NH_2$ | OH | H | $CH_2OH$ |
| neomycin B | $NH_2$ | $NH_2$ | H | $CH_2NH_2$ |
| neomycin C | $NH_2$ | $NH_2$ | $CH_2NH_2$ | H |
| paromomycin I | OH | $NH_2$ | H | $CH_2NH_2$ |
| paromomycin II | OH | $NH_2$ | $CH_2NH_2$ | H |

|  | $R_1$ | $R_2$ |
|---|---|---|
| Bu-2659E | OH | D-ribose |
| ribostamycin | $NH_2$ | D-ribose |
| Bu-2659 DP-I | OH | H |
| neamine | $NH_2$ | H |

Actinomycete Strain No. J296-21 was isolated from a soil sample collected in the Philippines. It has been deposited in the American Type Culture Collection, Washington, D.C., and added to its collection of microorganisms as ATCC No. 39150.

Strain No. J296-21 forms aerial and substrate mycelia, and the color of the aerial mycelium is white, later turning to gray. It forms coiled spore-chains on monopodially branched aerial sporophores, each containing 10 to 50 arthrospores in a chain. A tightly coiled sporechain is often formed. The spores are oval in shape, 0.6–0.8 by 0.9–1.2 μm in size, and have a rugose or smooth surface. The spirals of the spore-chains often coalesce as dark, moist masses.

Strain J296-21 grows well and forms aerial mycelium in both nutritionally rich organic media and chemically defined agar media except for ISP No. 6 Medium. Strain J296-21 does not produce melanoid pigment in tryptone-yeast extract broth (ISP No. 1), peptone-yeast extract-iron agar (ISP No. 6) or tyrosine agar (ISP No. 7). It grows on agar medium containing NaCl at a concentration of 6% but not at 8%. Whorl sporophores, motile spores and sporangia were not observed in any of the media examined. The cultural and physiological characteristics of strain J296-21 are shown in Table 1 and 2, respectively. The pattern of carbohydrate utilization is shown in Table 3.

The above-mentioned characteristics of strain J296-21 indicate that it belongs to the genus Streptomyces. According to the descriptions in Bergey's Manual of Determinative Bacteriology, 8th ed., strain J296-21 resembles the species group, > pirales, gray series, non-chromogenic, and smooth spore surface, which includes 65 species and 7 subspecies. Hygroscopic change of the aerial mycelium (blackening and moistening) is an additional important property of strain J296-21. Dietz ["Criteria for Characterization of Hygroscopicus Strains" in *Actinomycetes: The Boundary Microorganisms*, edit. T. Arai, Toppan Co. Ltd., Japan pp. 183-191 (1976)] classified hygroscopic Streptomyces strains into two species, *S. hygroscopicus* and *S. neohygroscopicus*. Based on the descriptions in the Bergey's Manual and the studies of Dietz, strain J296-21 was determined to belong to the species, *Streptomyces hygroscopicus*.

TABLE 1

Cultural Characteristics of Strain J296-21

| | |
|---|---|
| Czapek's sucrose-nitrate agar | G: Abundant |
| | R: White (263) to light gray (264) |
| | A: Abundant, light gray (264) to medium gray (265) |
| | D: None |
| Tryptone-yeast extract agar (ISP No. 1) | moderately floccose, sedimented, not pigmented |
| Yeast extract-malt extract agar (ISP No. 2) | G: Abundant |
| | R: Moderate orange yellow (71) to deep yellowish brown (75) |
| | A: Moderate, white (263) |
| | D: None |
| Oat meal agar (ISP No. 3) | G: Abundant |
| | R: White (263) to light gray (264) |
| | A: Abundant, white (263) to medium gray (265), hygroscopic |
| | D: None |
| Inorganic salts-starch agar (ISP No. 4) | G: Abundant |
| | R: White (263) to light gray (264) |
| | A: Abundant, light gray (264) to dark gray (266), hygroscopic |
| | D: None |
| Glycerol-asparagine agar (ISP No. 5) | G: Abundant |
| | R: Light yellow (86) to strong yellow (84) |
| | A: Abundant, white (263) to light brownish gray (63), hygroscopic |
| | D: Light greenish yellow (101) |
| Peptone-yeast extract-iron agar (ISP No. 6) | G: Moderate |
| | R: Pale yellow (89) |
| | A: None |
| | D: None |
| Tyrosine agar (ISP No. 7) | G: Abundant |
| | R: Strong reddish brown (40) |
| | A: Abundant, white (263) to yellowish white (92) |
| | D: Dark orange yellow (72) |
| Bennett's agar | G: Abundant |
| | R: Pale yellow (89) to dark yellow (88) |
| | A: Abundant, white (263) to medium gray (265), hygroscopic |
| | D: None |

Abbreviations
G: Growth
R: Reverse color
A: Formation of aerial mycelium and aerial mass color
D: Diffusible pigment
Colors and numbers in parentheses follow the color standard described by K. L. Kelly and D. B. Judd: ISCC-NBS color-name charts illustrated with centroid colors. U.S. Dept. of Comm. Circ. 553, Washington, D.C., Nov., 1975.

TABLE 2

Physiological Reactions

| Test | Strain No. J296-21 | S. hygroscopicus (NRRLB-1340) | Methods and Materials |
|---|---|---|---|
| Nitrite from nitrate | Positive | Negative | Inorganic medium: Czapek's glucose nitrate broth. |
| | Positive | Negative | Organic medium: 0.5% yeast extract, 1% glucose, 0.5% KNO$_3$, 0.1% CaCO$_3$. |
| Sodium chloride tolerance | Moderate growth at 0.5% NaCl. Restricted growth at 1.0–6.0% NaCl. No growth at 8% NaCl. | Moderate growth at 1.5% NaCl. Restricted growth at 8.0% NaCl. | Basal medium: 1% yeast extract, 2% soluble starch, 1.5% agar. |
| Casein hydrolysis in agar medium | Weakly positive (1–2 mm hydrolyzed band after 7 days). | Positive (3–5 mm hydrolyzed band after 7 days). | Luedemann's-agar medium.* |
| Reactions in skimmed milk solution | Not coagulated and completely peptonized. | Not coagulated and completely peptonized. | |
| Gelatin stab | Liquefied | Liquefied | |
| Formation of melanoid | Negative | Negative | Tyrosine agar and peptone-yeast-iron agar and tryptone-yeast extract broth. |
| Effect of temperature | Maximal growth at 28–37° C. Moderate growth at 20° C. and | Maximal growth at 28–37° C. Moderate growth at 20° C. No | Yeast extract-malt extract agar. |

TABLE 2-continued

| | Physiological Reactions | | |
|---|---|---|---|
| Test | Strain No. J296-21 | S. hygroscopicus (NRRLB-1340) | Methods and Materials |
| | 43° C. No growth at 5° C. and 45° C. | growth at 5° C. and 43° C. | |

*Luedemann, G. M., Intl. J. Syst. Bacteriol. 21: 240–247, 1971.

TABLE 3

| | Carbohydrate Utilization | |
|---|---|---|
| | Strain J296-21 | S. hygroscopicus NRRLB-1340 |
| Glycerol | + | + |
| D(−)-Arabinose | + | − |
| L(+)-Arabinose | + | + |
| D-Xylose | + | + |
| D-Ribose | + | + |
| L-Rhamnose | + | − |
| D-Glucose | + | + |
| D-Galactose | + | + |
| D-Fructose | + | + |
| D-Mannose | + | + |
| L(−)-Sorbose | − | − |
| Sucrose | − | − |
| Lactose | + | − |
| Cellobiose | + | + |
| Melibiose | + | − |
| Trehalose | + | + |
| Raffinose | + | − |
| D(+)-Melezitose | − | − |
| Soluble starch | + | + |
| Cellulose | + | − |
| Dulcitol | − | − |
| Inositol | + | − |
| D-Mannitol | + | + |
| D-Sorbitol | + | − |
| Salicin | + | + |

Basal medium: Pridham-Gottlieb's inorganic medium

Antibiotic complex Bu-2659 is produced by cultivating *Streptomyces hygroscopicus* Strain No. J296-21 under submerged aerobic conditions in an aqueous nutrient medium. The general procedures used for the culture of other actinomycetes are applicable to the cultivation of *Streptomyces hygroscopicus* Strain J296-21. The nutrient medium should contain one or more assimilable carbon sources such as glycerol, glucose, fructose, mannose, starch, dextrin, maltose, molasses, oil, fats and the like, either in purified or the crude state. The nutrient medium should also contain one or more assimilable nitrogen sources such as, for example, soybean meal, fish meal, malt extract, peptone, yeast extract, distiller's solubles, gluten meal, cornsteep liquor, cottonseed flour, casein, hydrolyzed protein substances, nitrates, ammonium salts, urea and the like. Nutrient inorganic salts such as sodium chloride, potassium phosphate, magnesium sulfate, calcium carbonate, and trace amounts of heavy metal salts such as copper, zinc, manganese, iron, and the like, may also be added to the medium. In the aerated submerged culture an antifoam such as liquid paraffin, soybean oil, fat or silicone may be utilized.

The fermentation temperature preferably should be in the range of from about 20° C. to about 43° C., and the most preferred range is from about 28° C. to about 37° C. The pH of the fermentation medium should be in the range of from about 5 to about 10, and preferred range is from about 6 to about 8. Ordinarily, optimum antibiotic production is obtained in 4 to 7 days, during which the pH gradually rises to about 8-8.5.

When a tank fermentation is to be carried out, it is desirable to produce a vegetative inoculum in a nutrient broth by inoculating the broth culture with, for example, a slant culture or lyophilized culture of the organism. After obtaining an active inoculum in this manner, it is transferred aseptically to the fermentation tank medium. The antibiotic activity in the fermentation broth may be determined by the paper disc-agar diffusion method using *Bacillus subtilis* PCI 219 as the test organism.

After optimum broth potency (typically 300–350 mcg/mL) is obtained, the fermentation broth is filtered, preferably with filter aid. The mycelial cake usually is washed with water, and the combined filtrate and washings are then adjusted to a pH of about 7.0 and adsorbed on a column of resin such as Amberlite IRC-50 ($NH_4^+$). It is developed with dilute $NH_4OH$ and the active eluate fractions are combined and concentrated. The concentrated Bu-2659 complex may then be separated into its components by chromatography on a resin such as Amberlite CG-50 ($NH_4^+$), using increasing concentrations of dilute $NH_4OH$ for development. This procedure sometimes gives a mixture of components D and E. That mixture may, if desired, be separated by silica gel column chromatography using $CH_3OH$-$NH_4OH$-$H_2O$ as the solvent system.

Bu-2659 complex and the individual components thereof are usually obtained in their free base form, but may be converted to their acid addition salts by reaction with an acid in a conventional manner. This invention includes within its scope the pharmaceutically acceptable acid addition salts of Bu-2659 complex and its individual components. The pharmaceutically acceptable acid addition salts of Bu-2659 complex and its individual components include, for example, those obtained by reaction with an inorganic acid such as hydrochloric, hydrobromic, sulfuric, phosphoric, nitric or the like, as well as with an organic acid such as acetic, malic, citric, ascorbic, methanesulfonic or the like.

The sulfates of Bu-2659 components are freely soluble in water, slightly soluble in methanol and ethanol but practically insoluble in n-butanol, acetone and other organic solvents. They give positive reactions with ninhydrin and anthrone reagents, but are negative in the Tollens, Fehling and Sakaguchi reactions. The thin layer chromatograms (TLC) of the Bu-2659 components are shown in Table 4 compared with those of neomycin, paromomycin and ribostamycin.

TABLE 4

| | TLC of Bu-2659 A, B, C, D and E | | | | | | | |
|---|---|---|---|---|---|---|---|---|
| | Rf Value (by ninhydrin reagent) | | | | | | | |
| Sys- | Bu-2659 | | | | | Neo- | Paro-mo- | Ribo-sta- |
| tem* | A | B | C | D | E | mycin | mycin | mycin |
| S-110 | 0.31 | 0.35 | 0.39 | 0.43 | 0.43 | 0.23 | 0.33 | 0.33 |
| S-115S | 0.47 | 0.54 | 0.54 | 0.63 | 0.60 | 0.40 | 0.51 | 0.52 |
| S-115A | — | — | — | 0.57 | 0.06 | — | — | 0.11 |

Figure 1:
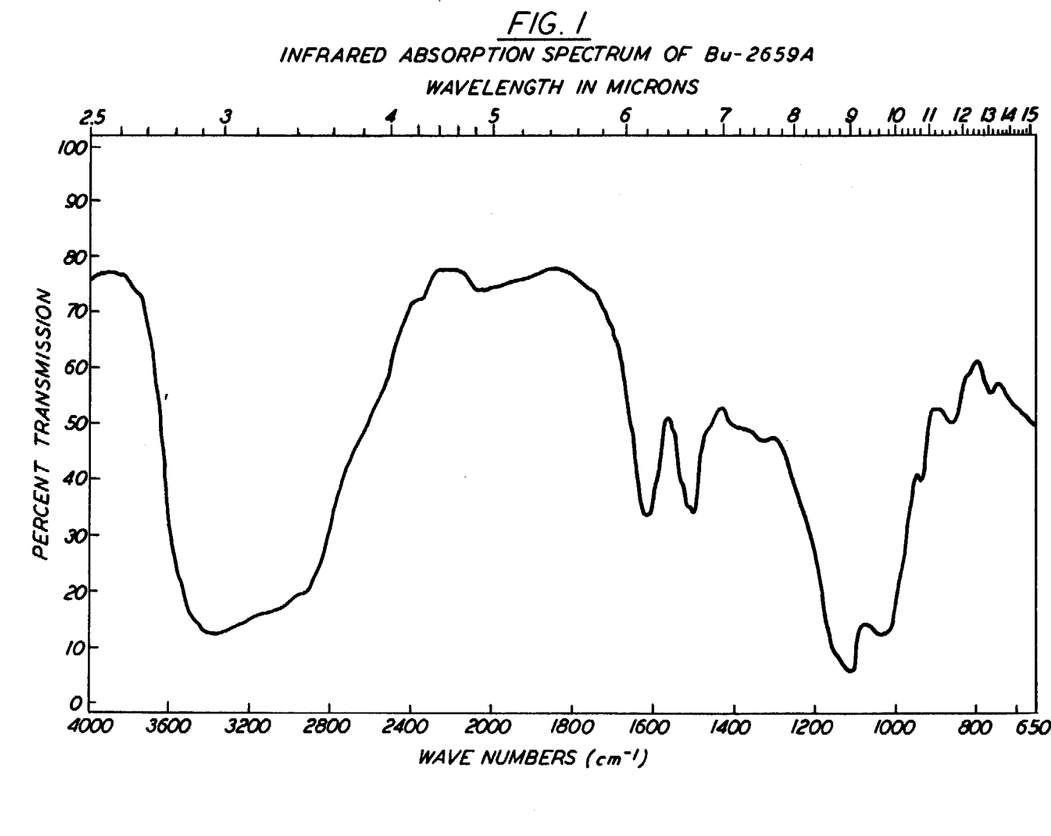
FIG. 1 shows the infrared absorption spectrum of Bu-2659A when pelleted in KBr.
Figure 2:
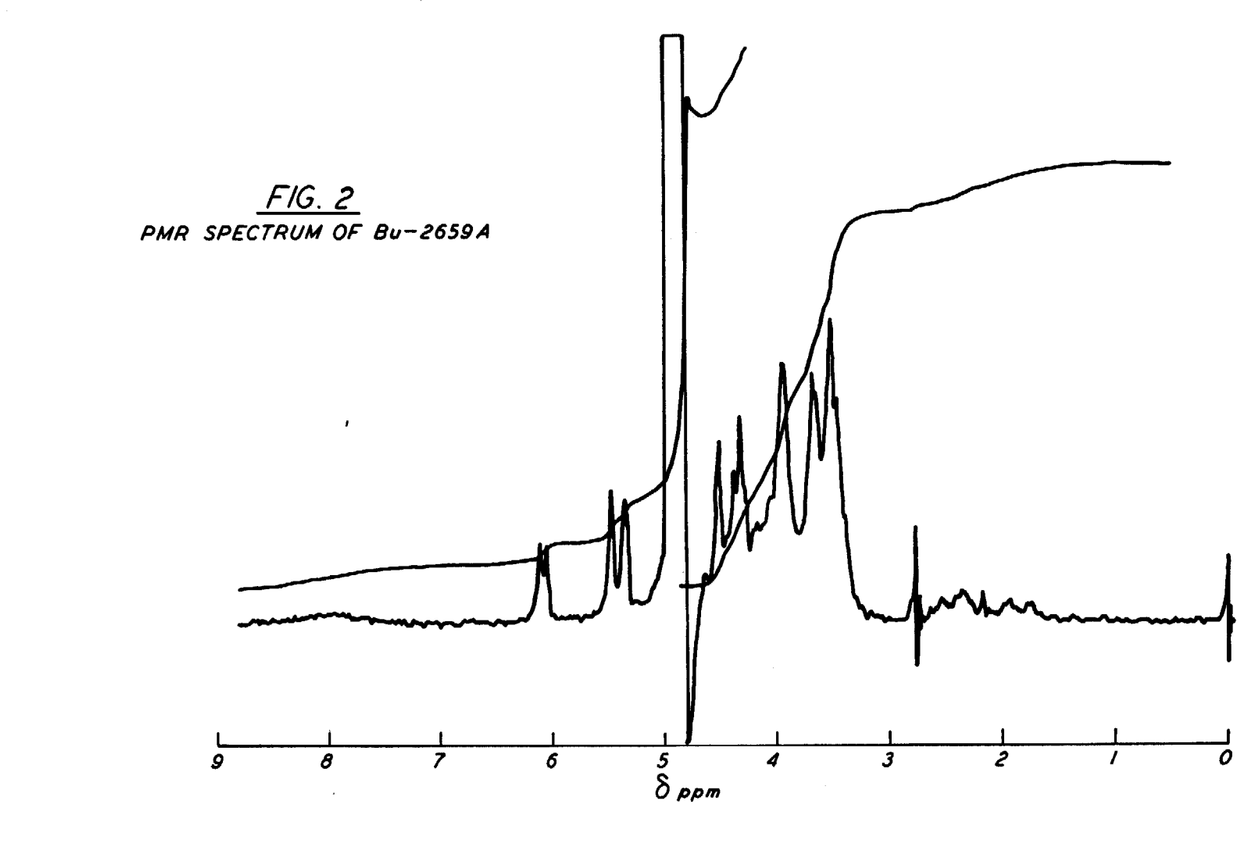
FIG. 2 shows the Proton Magnetic Resonance (PMR) spectrum of Bu-2659A in $D_2O$ (60 MHz).
Figure 3:
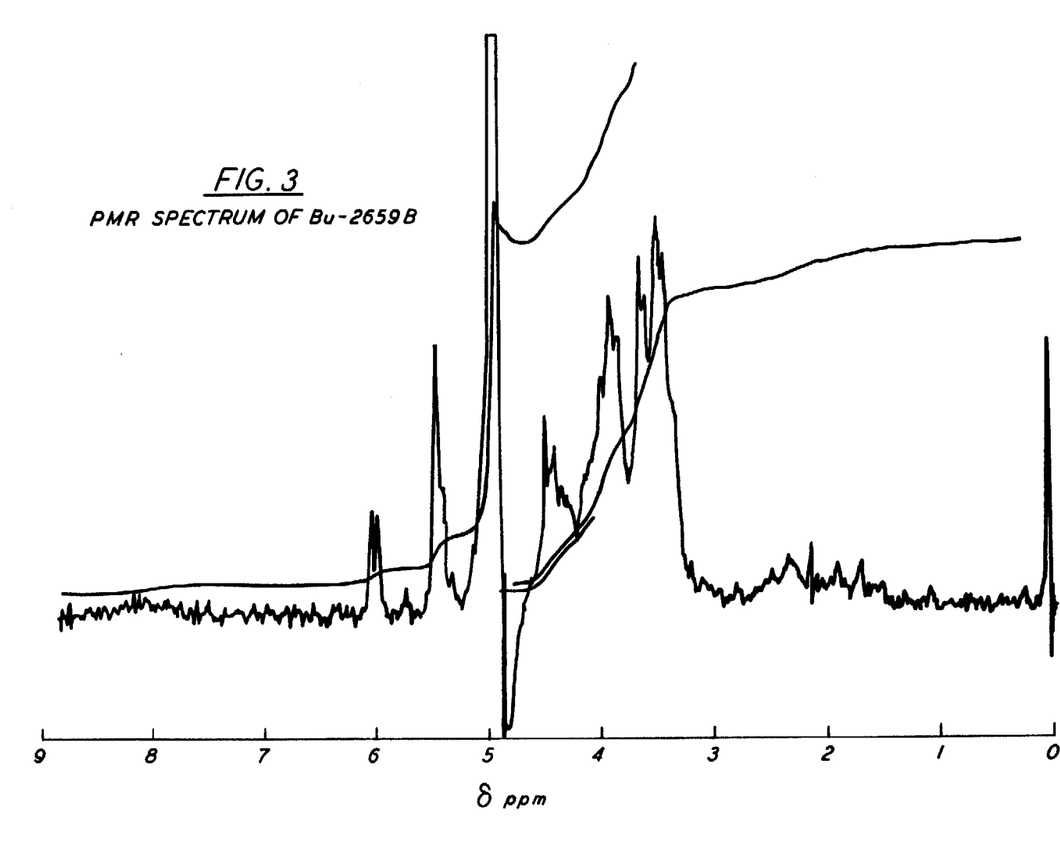
FIG. 3 shows the Proton Magnetic Resonance (PMR) spectrum of Bu-2659B in $D_2O$ (60 MHz).
Figure 4:
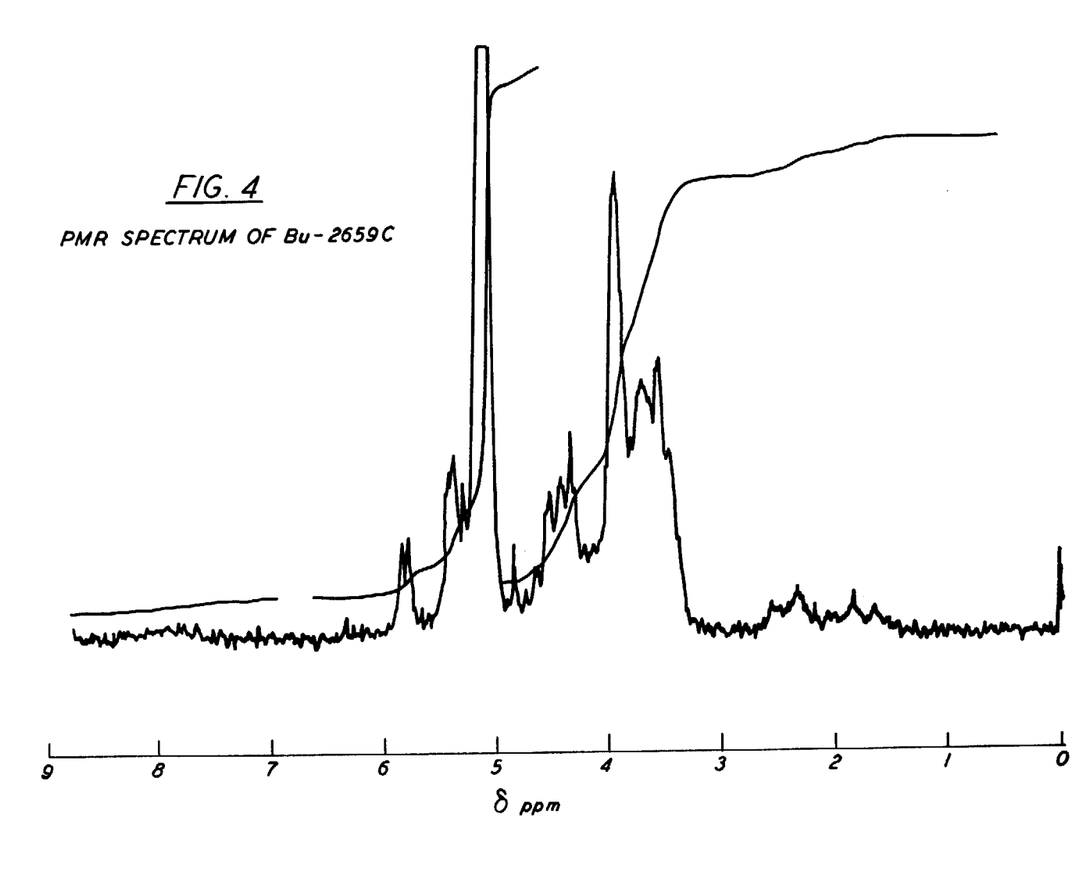
FIG. 4 shows the Proton Magnetic Resonance (PMR) spectrum of Bu-2659C in $D_2O$ (60 MHz).
Figure 5:
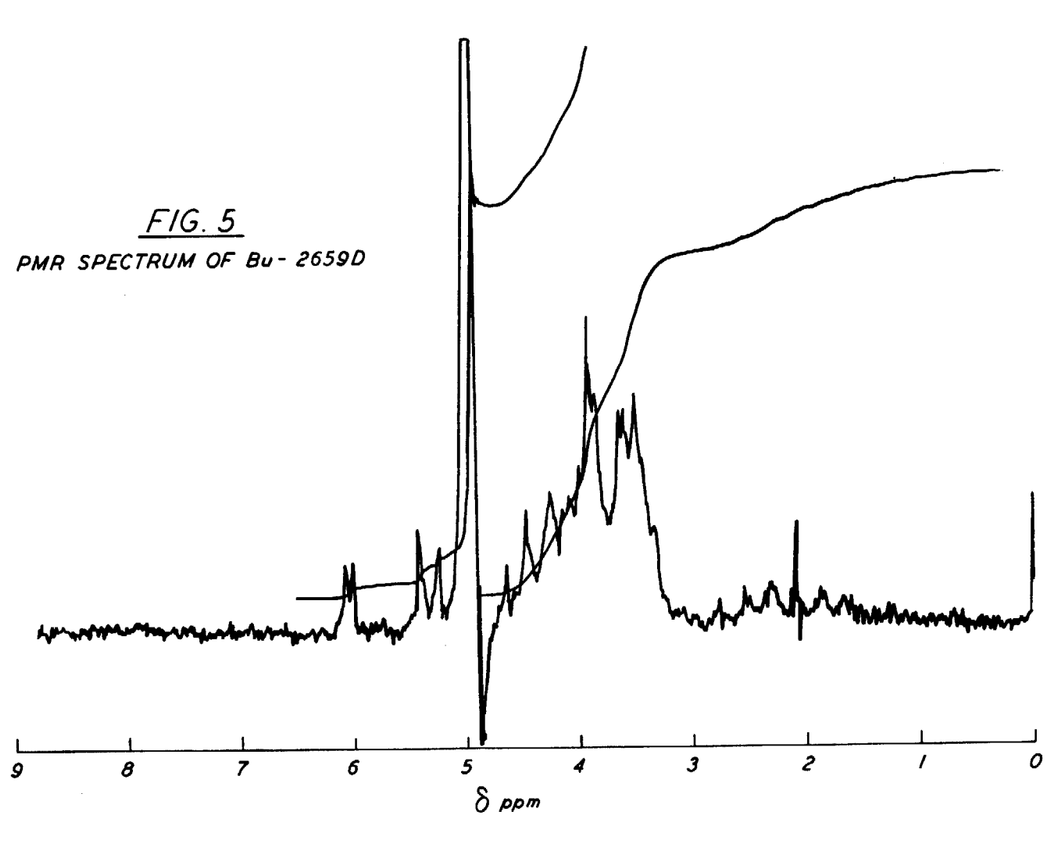
FIG. 5 shows the Proton Magnetic Resonance (PMR) spectrum of Bu-2659D in $D_2O$ (60 MHz).
Figure 6:
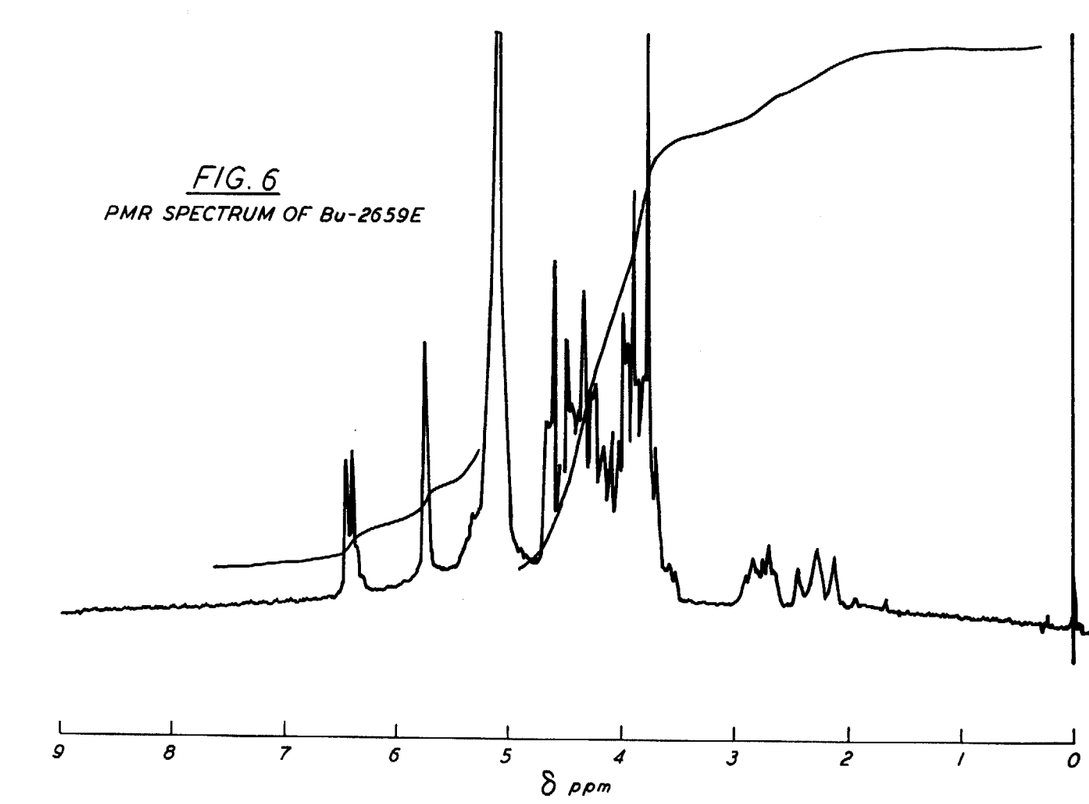
FIG. 6 shows the Proton Magnetic Resonance (PMR) spectrum of Bu-2659E in $D_2O$ (80 MHz).

*S-110: $SiO_2$ plate, $CHCl_3$—$CH_3OH$—conc. $NH_4OH$—$H_2O$ (1:4:2:1)
S-115S: $SiO_2$ plate, $CHCl_3$—$CH_3OH$—17% $NH_4OH$ (2:1:1, upper layer)
S-115A: $Al_2O_3$ plate, solvent system same as S-115S The physico-chemical properties of the sulfates of Bu-2659A, B, C, D and E are summarized in Table 5. The Bu-2659 components exhibit only end absorption in the UV spectra. The IR spectrum of Bu-2659A (FIG. 1) is very similar to that of components B, C, D and E, showing characteristics of the spectra of aminoglycoside antibiotics such as neomycin, paromomycin and ribostamycin. The proton NMR spectra of Bu-2659 components A, B, C, D and E are shown in FIGS. 2 through 6, respectively. The presence of three anomeric protons was indicated in the NMR spectra of Bu-2659 components A, B, C and D, while two anomeric protons were observed in the spectrum of component E (Table 5).

Hinton agar medium (Difco) was generally used for the MIC determination for most test organisms, GC medium (Eiken) for fastidious bacteria such as streptococci, *Neisseria* and *Haemophilus* species, and No. 1001 agar medium [3% glycerol, 0.3% sodium L-glutamate, 0.2% peptone, 0.31% $Na_2HPO_4$, 0.1% $KH_2PO_4$, 0.005% ammonium citrate, 0.001% $MgSO_4$, 1.5% agar] for mycobacteria. Reference antibiotics utilized in these tests included commercially available neomycin as well as its components, neomycins B and C [as used herein, the term "neomycin" means the commercial product containing neomycins B and C at an approximate ratio of 7:3], paromomycin [the commercial product containing <90% of paromomycin I and <10% of paromomy-

TABLE 5

Physico-chemical Properties of Bu-2659 Components (Sulfates)

| | Bu-2659A | | Bu-2659B | | Bu-2659C | | Bu-2659D | | Bu-2659E | |
|---|---|---|---|---|---|---|---|---|---|---|
| Nature | white amorphous solid | | white amorphous solid | | white amorphous solid | | white amorphous solid | | white amorphous solid | |
| Mp (°C.) | 210~215 (dec.) | | 200~206 (dec.) | | 195~201 (dec.) | | 193~204 (dec.) | | 195~218 (dec.) | |
| $[\alpha]_D$ ($H_2O$)** | +52° (c = 0.6) | | +73° (c = 0.6) | | +55° (c = 0.6) | | +52.5° (c = 0.6) | | +47° (c = 0.37) | |
| Molecular formula | $C_{23}H_{45}N_5O_{14}$ | | $C_{23}H_{45}N_5O_{14}$ | | $C_{23}H_{44}N_4O_{15}$ | | $C_{23}H_{44}N_4O_{15}$ | | $C_{17}H_{33}N_3O_{11}$ | |
| Elemental analysis | $C_{23}H_{45}N_5O_{14}$ .2.5$H_2SO_4$.2$H_2O$ | | $C_{23}H_{45}N_5O_{14}$ .2.5$H_2SO_4$.2.5$H_2O$ | | $C_{23}H_{44}N_4O_{15}$ .2$H_2SO_4$.3$H_2O$ | | $C_{23}H_{44}N_4O_{15}$ .2$H_2SO_4$.3$H_2O$ | | $C_{17}H_{33}N_3O_{11}$ .1.5$H_2SO_4$.2.5$H_2O$ | |
| | Calc'd | Found | Calc'd | Found | Calc'd | Found | Calc'd | Found | Calc'd | Found |
| C % | 30.81 | 30.94 | 30.50 | 30.57 | 31.87 | 31.89 | 31.87 | 31.50 | 31.53 | 31.24 |
| H % | 6.07 | 6.62 | 6.12 | 6.35 | 6.28 | 6.29 | 6.28 | 6.15 | 6.38 | 6.34 |
| N % | 7.81 | 8.01 | 7.73 | 7.52 | 6.46 | 6.27 | 6.46 | 6.83 | 6.49 | 6.60 |
| S % | 8.92 | 9.23 | 8.83 | 8.68 | 7.40 | 7.46 | 7.40 | 7.79 | 7.43 | 7.65 |
| NMR spectrum* (δ, ppm) | 1.5~2.7 (2H,m) | | 1.4~2.7 (2H,m) | | 1.5~2.7 (2H,m) | | 1.5~2.6 (2H,m) | | 2.14 (1H,q,J = 12) | |
| | 3.1~4.7 (22H,m) | | 3.1~4.7 (22H,m) | | 3.2~4.8 (22H,m) | | 3.0~4.7 (22H,m) | | 2.75 (1H,dt,J = 12,4.0) | |
| | 5.35 (1H,br.s) | | 5.40 (2H,br.s) | | 5.35 (1H,br.s) | | 5.25 (H,br.s) | | 3.5~4.7 (16H,m) | |
| | 5.47 (1H,br.s) | | 5.95 (1H,d,J = 3.6) | | 5.40 (1H,br.s) | | 5.42 (1H,br.s) | | 5.76 (1H,s) | |
| | 6.09 (1H,d,J = 3.6) | | | | 5.80 (1H,d,J = 3.6) | | 6.02 (1H,d,J = 4.0) | | 6.43 (1H,d,J = 4.0) | |

*60 MHz in $D_2O$, Pd < 2.0 for Bu-2659A, B, C and D. 80 MHz in $D_2O$ at PD 4.6 for Bu-2659E. TMS was used as external standard. Abbreviations: s: singlet, d: doublet, t: triplet, q: quartet m: multiplet, br.: broad, dt: double triplet. Coupling constant (J) given in Hz.
**Temperature of $[\alpha]_D$ determination: A 27° C.; B 25° C.; C 25° C.; D 25° C.; E 26° C.

Bu-2659A (1.56 g) was hydrolyzed with 0.4N methanolic hydrogen chloride (455 mL) at reflux temperature for 4 hours. The hydrolyzate was chromatographed on a column of CG-50 ($NH_4^+$, 360 mL) to afford a bioactive degradation product designated as Bu-2659 DP-I (657 mg). The structure of this compound has been determined to be 1-deamino-1-hydroxyneamine (see Formula II). The TLC of Bu-2659 DP-I is shown in Table 6 compared with that of neamine.

TABLE 6

TLC of Bu-2659 DP-I and Neamine

| | Rf Value (by ninhydrin) | |
|---|---|---|
| System* | Bu-2659 DP-I | Neamine |
| S-110 | 0.55 | 0.48 |
| S-108 | 0.47 | 0.32 |
| S-123 | 0.48 | 0.24 |

*S-108: $SiO_2$ plate, Acetone—AcOH—$H_2O$ (20:6:74)
S-123: $SiO_2$ plate, 10% $AcONH_4$—$CH_3OH$—10% $NH_4OH$ (9:10:1)

The minimum inhibitory concentrations (MIC) of Bu-2659A, B, C, D and E were determined for a variety of gram-positive and gram-negative bacteria by the serial two-fold agar dilution method using the Steer's multi-inoculating apparatus. The inoculm was standardized as a $10^4$ dilution of an overnight culture of the test organisms in Heart Infusion Broth (Difco). Mueller-cin II] and ribostamycin.

The in vitro antibacterial spectra of the Bu-2659 components are shown in Table 7. Bu-2659A showed the highest activity among the five Bu-2659 components, its activity being comparable to that of neomycin. Bu-2659B and C were approximately ¼ as active as Bu-2659A, while Bu-2659D and E were less active than components B and C. It was surprising to find that Bu-2659A has substantially the same level of antibacterial activity as neomycin B (which is the 2-deoxystreptamine-containing congener or Bu-2659A, since the 1-deamino-1-hydroxy analogs of aminoglycoside antibiotics reported to date are generally less active than their parent antibiotics.

Bu-2659 complex and its components A, B, C, D and E are antibiotics which are useful in the treatment of bacterial infections in mammals, including man. They may be utilized orally, parenterally or topically, and may be administered alone or in conjunction with other active ingredients. The preferred component is Bu-2659A. It may be administered in the amounts and the dosage forms commonly utilized for neomycin. Components B, C, D and E may be utilized in the same dosage forms and are used in amounts appropriate to their bioactivity.

TABLE 7

Antibacterial Activities of Bu-2659 Components

| Test Organism | Bu-2659 A | B | C | D | E | Neomycin * | B | C | Paromo-mycin | Ribosta-mycin |
|---|---|---|---|---|---|---|---|---|---|---|
| *Staphylococcus aureus* 209P | 0.8 | 3.1 | 3.1 | 6.3 | 25 | 0.4 | 0.4 | 0.8 | 0.8 | 1.6 |
| *Staphylococcus aureus* Smith | 1.6 | 3.1 | 6.3 | 25 | 50 | 0.8 | 0.4 | 1.6 | 1.6 | 3.1 |
| *Staphylococcus aureus* D136 | 0.8 | 6.3 | 6.3 | 25 | 50 | 0.8 | 0.4 | 1.6 | 0.8 | 3.1 |
| *Micrococcus luteus* PCI 1001 | 3.1 | >100 | >100 | 100 | >100 | 0.8 | 0.8 | 50 | 6.3 | 6.3 |
| *Micrococcus flavus* D12 | 6.3 | >100 | >100 | 100 | >100 | 3.1 | 1.6 | 100 | 12.5 | 12.5 |
| *Bacillus subtilis* PCI 219 | 0.1 | 0.4 | 0.8 | 1.6 | 3.1 | <0.05 | <0.05 | <0.05 | 0.2 | 0.4 |
| *Escherichia coli* NIHJ | 1.6 | 12.5 | 6.3 | 12.5 | 50 | 1.6 | 1.6 | 3.1 | 3.1 | 3.1 |
| *Escherichia coli* Juhl | 3.1 | 50 | 25 | 50 | >100 | 3.1 | 3.1 | 12.5 | 12.5 | 6.3 |
| *Klebsiella pneumoniae* D11 | 0.2 | 1.6 | 1.6 | 1.6 | 12.5 | 0.4 | 0.2 | 0.4 | 0.4 | 0.4 |
| *Proteus vulgaris* A9436 | 0.4 | 3.1 | 1.6 | 3.1 | 12.5 | 0.8 | 0.8 | 1.6 | 0.8 | 0.8 |
| *Proteus mirabilis* A9554 | 0.8 | 6.3 | 3.1 | 6.3 | 12.5 | 0.8 | 0.8 | 3.1 | 0.8 | 1.6 |
| *Proteus mirabilis* A9906 | 0.8 | 6.3 | 3.1 | 6.3 | 25 | 0.8 | 0.8 | 1.6 | 0.8 | 1.6 |
| *Proteus morganii* A9553 | 1.6 | 12.5 | 6.3 | 12.5 | 25 | 3.1 | 3.1 | 3.1 | 1.6 | 1.6 |
| *Proteus rettgeri* A15167 | 0.8 | 3.1 | 3.1 | 3.1 | 12.5 | 1.6 | 1.6 | 1.6 | 1.6 | 0.8 |
| *Pseudomonas aeruginosa* D15 | 3.1 | >100 | 25 | >100 | >100 | 3.1 | 3.1 | >100 | 50 | >100 |
| *Pseudomonas aeruginosa* A9930 | 1.6 | >100 | 12.5 | 50 | >100 | 3.1 | 3.1 | 50 | 12.5 | 100 |
| *Serratia marcescens* A20019 | 3.1 | 100 | 6.3 | 100 | >100 | 1.6 | 1.6 | 6.3 | 1.6 | 25 |

* commercial product (neomycin B:C = ca. 7:3)

The antibacterial activity of Bu-2659A against strains of Streptococcus, Neisseria, Haemophilus and Mycobacterium is shown in Table 8. Bu-2659A and neomycin showed equivalent activity against the species of Streptococcus and Mycobacterium, while Bu-2659A was more active than neomycin against Neisseria and Haemophilus species.

TABLE 8

Antibacterial Activities of Bu-2659A

| Test Organisms | Media | MIC (mcg/mL) Bu-2659A | Neomycin |
|---|---|---|---|
| *Streptococcus pyogenes* A20201 | GC | 25 | 12.5 |
| *Streptococcus pneumoniae* Type I | " | 25 | 25 |
| *Neisseria gonorrhoeae* A20143 | " | 50 | >400 |
| *Neisseria meningitidis* A21496 | " | 50 | 400 |
| *Haemophilus influenzae* A9729 | " | 50 | 400 |
| *Mycobacterium smegmatis* 607 | No. 1001 | 0.4 | 0.4 |
| *Mycobacterium phlei* | " | 0.1 | 0.2 |
| *Mycobacterium ranae* | " | 0.4 | 0.4 |

A series of aminoglycoside resistant organisms which have been shown to produce aminoglycoside-modifying enzymes were examined for their susceptibility toward Bu-2659A and reference antibiotics. The results are shown in Table 9. Bu-2659A was more active than neomycin, paromomycin and ribostamycin against several resistant strains which produce APH(3') or AAC(3).

TABLE 9

Activities of Bu-2659A and Reference Antibiotics Against Aminoglycoside-Resistant Organisms

| Test Organism | Inactivating** Enzyme | MIC* (mcg/mL) Bu-2659A | Neomycin | Paromo-mycin | Ribosta-mycin |
|---|---|---|---|---|---|
| *Staphylococcus aureus* A20239 | APH(3')-I,II | 12.5 | 25 | >100 | >100 |
| *Bacillus brevis* IFO 12334 | ANT(4') | >100 | 25 | >100 | >100 |
| *Escherichia coli* ML 1630 | APH(3')-I | >100 | >100 | >100 | >100 |
| *Escherichia coli* A20107 | APH(3')-II | 25 | 100 | >100 | >100 |
| *Escherichia coli* JR66/W677 | APH(3')-II ANT(2") | >100 | >100 | >100 | >100 |
| *Escherichia coli* JR88 | AAC(3)-I | 1.6 | 1.6 | 1.6 | 1.6 |
| *Escherichia coli* JR35/C600 | APH(3')-I | 25 | >100 | >100 | >100 |
| *Escherichia coli* A20732 | ANT(2") | 0.8 | 0.8 | 1.6 | 1.6 |
| *Escherichia coli* NR79/W677 | AAC(6')-I | 50 | 50 | >100 | >100 |
| *Enterobacter cloacae* A20364 | APH(3')-I | 50 | >100 | >100 | >100 |
| *Pseudomonas aeruginosa* A20601 | AAC(3)-I APH(3')-II | 6.3 | 12.5 | >100 | >100 |
| *Pseudomonas aerug-* | AAC(3)-II | >100 | >100 | >100 | >100 |

TABLE 9-continued

| | | MIC* (mcg/mL) | | | |
|---|---|---|---|---|---|
| Test Organism | Inactivating** Enzyme | Bu-2659A | Neomycin | Paromo- mycin | Ribosta- mycin |

Activities of Bu-2659A and Reference Antibiotics Against Aminoglycoside-Resistant Organisms

*inosa* A20896

*Mueller-Hinton agar (Difco)
**APH: aminoglycoside phosphotransferase
ANT: aminoglycoside nucleotidyltransferase
AAC: aminoglycoside acetyltransferase The in vitro activity of Bu-2659 DP-I (1-deamino-1-hydroxyneamine) is shown in Table 10 along with that of neamine. In contrast to the structure-activity relationship observed with Bu-2659A and neomycin, the degradation product of Bu-2659A was much less active than neamine, the corresponding bioactive fragment derived from neomycin.

TABLE 10

Antibacterial Spectrum of Bu-2659 DP-I and Neamine

| | MIC (mcg/mL)* | |
|---|---|---|
| Test Organisms | Bu-2659 DP-I | Neamine |
| *Staphylococcus aureus* 209P | 200 | 6.3 |
| *Staphylococcus aureus* Smith | 200 | 3.1 |
| *Bacillus subtilis* PCI 219 | 100 | 3.1 |
| *Escherichia coli* NIHJ | 200 | 12.5 |
| *Escherichia coli* JR88 | 200 | 12.5 |
| *Klebsiella pneumoniae* D11 | 200 | 12.5 |
| *Proteus vulgaris* A9436 | 200 | 6.3 |
| *Proteus mirabilis* A9554 | 800 | 25 |
| *Pseudomonas aeruginosa* A9930 | >800 | 400 |

*Mueller-Hinton agar

The in vivo activity of Bu-2659A was assessed by experimental systemic infection in mice. The pathogenic bacteria used in the in vivo tests were E. coli Juhl, K. pneumoniae D-11, P. mirabilis A9906, S. aureus Smith and S. pyogenes A20201. Mice were challenged intraperitoneally with approximately $100 \times LD_{50}$ dose of the pathogens in a 5% suspension of hog gastric mucin (American Laboratories, Omaha, Neb.). A single intramuscular treatment with the antibiotic was given immediately after the bacterial challenge. Five mice were used for each dosage level and the animals were observed for 4 days to determine the median protective dose ($PD_{50}$). Neomycin was comparatively tested as a reference compound. As shown in Table 11, Bu-2659A afforded excellent protection in mice against the five experimental infections tested. Bu-2659A showed in vivo activity comparable to that of neomycin against infections with three gram-negative bacteria. In terms of $PD_{50}$ value Bu-2659A was about one-half as active as neomycin against infections with S. aureus and S. pyogenes.

TABLE 11

In vivo Activity of Bu-2659A

| | $PD_{50}$ (mg/kg, im) | |
|---|---|---|
| Test Organisms | Bu-2659A | Neomycin |
| *Escherichia coli* Juhl | 3.1 | 3.1 |
| *Klebsiella pneumoniae* D-11 | 1.1 | 0.9 |
| *Proteus mirabilis* A9906 | 2.5 | 1.8 |
| *Staphylococcus aureus* Smith | 0.63 | 0.31 |
| *Streptococcus pyogenes* A20201 | 50 | 50 |

The acute toxicity of Bu-2659A was determined in mice by intravenous, intraperitoneal and subcutaneous routes. Neomycin also was tested for comparison purposes. As shown in Table 12, Bu-2659A was significantly less toxic than neomycin by all routes of administration. The toxicity of Bu-2659A was approximately ⅓ that of neomycin in terms of $LD_{50}$ values, thus presenting a potential clinical advantage for Bu-2659A.

TABLE 12

Acute Toxicities of Bu-2659A

| | $LD_{50}$ (mg/kg) | | |
|---|---|---|---|
| | intravenous | intraperitoneal | subcutaneous |
| Bu-2659A | 110 | 460 | 720 |
| Neomycin | 34 | 180 | 280 |

EXAMPLE 1

Preparation of Seed Culture and Small Scale Shake Flask Fermentations

A well-grown agar slant culture of the Bu-2659 producing organism, Strain No. J296-21, was inoculated into a 500-mL Erlenmeyer flask containing 100 mL of seed medium composed of malt extract 2%, fish meal 2%, peptone 0.2%, NaCl 0.5%, $CaCO_3$ 0.4% and $MgSO_4$ 0.05%. The pH was adjusted to 7.2 before sterilization. The seed culture was incubated at 28° C. for 96 hours on a rotary shaker (250 rpm), and 3 mL of the growth was transferred to 500-mL Erlenmeyer flasks containing 100 mL of production medium having the same composition as the seed medium. Upon shaking fermentation at 28° C., the broth pH gradually rost to 8.0-8.4 after 4-7 days and the antibiotic production reached a maximum of 300~350 mcg/mL. The antibiotic activity in the fermentation broth was determined by the paper disc-agar diffusion method using *Bacillus subtilis* PCI 219 as a test organism.

EXAMPLE 2

Isolation and Purification

A combined fermentation broth from shake flasks (32 liters, 300 mcg/mL) was filtered with filter aid and the filtrate was adjusted to pH 7.0 with 6N HCl. The antibacterial activity in the filtrate was adsorbed on a column of Amberlite IRC-50 ($NH_4^+$, 1.6 L). The column was washed with water (5 L) and then developed with 0.5N $NH_4OH$ solution (4 L). The active eluates were combined and concentrated in vacuo to a small volume, and the concentrate was chromatographed using a column of Amberlite CG-50 ($NH_4^+$, 1.0 L). The column was washed with water (2 L) and then developed with increasing concentrations of aqueous ammonia. A mixture of components B, C, D and E was eluted first with 0.21N $NH_4OH$ (3 L) followed by component A which was eluted with 0.43N $NH_4OH$ (4 L). The mixture of components B, C, D and E was separated by chromatography on Amberlite CG-50 ($NH_4^+$, 200 mL) column. A mixture of components D and E was eluted first with 0.1N $NH_4OH$ (0.5 ), then components B and C were eluted successively with 0.167 N (0.7 L) and 0.21 N (1.0 L) NH$_4$OH solutions, respectively. The mixture of components D and E was further separated into each component by silica gel column chromatography (Wakogel C-200, 40 g) using a solvent system of CH$_3$OH-conc. NH$_4$OH-H$_2$O (9:1:1). Yields for components A, B, C, D and E in the above experiment were 7,100 mg, 370 mg, 350 mg 40 mg and 20 mg, respectively.

The free base of Bu-2659A (1,150 mg) was dissolved in a small amount of water and the pH adjusted to 4.5 with diluted H$_2$SO$_4$. Addition of methanol to the solution yielded a white precipitate which was collected by filtration and dried in vacuo to give the sulfate of Bu-2659A (1,280 mg). The sulfates of other components were prepared in the same manner. The physico-chemical properties of Bu-2659A, B, C, D and E produced in this example are set forth in Table 5.

The structures of Bu-2659 components A, B, C, D and E are as shown in Formulae I and II above. For convenience, names of the components which show their relationship to known antibiotics are set forth below.

Bu-2659A 1-deamino-1-hydroxyneomycin B
Bu-2659B 1-deamino-1-hydroxyneomycin C
Bu-2659C 1-deamino-1-hydroxyparomomycin I
Bu-2659D 1,6'''-dideamino-1,6'''-dihydroxyneomycin B
Bu-2659E 1-deamino-1-hydroxyribostamycin

We claim:

1. Antibiotic Bu-2659 complex comprising a mixture of 1-deamino-1-hydroxyneomycin B, 1-deamino-1-hydroxyneomycin C, 1-deamino-1-hydroxyparomomycin I, 1,6'''-dideamino-1,6'''-dihydroxyneomycin B and 1-deamino-1-hydroxyribostamycin, or an acid addition salt thereof.

2. 1-Deamino-1-hydroxyneomycin B or a pharmaceutically acceptable acid addition salt thereof.

3. 1-Deamino-1-hydroxyneomycin C or a pharmaceutically acceptable acid addition salt thereof.

4. 1-Deamino-1-hydroxyparomomycin I or a pharmaceutically acceptable acid addition salt thereof.

5. 1,6'''-Dideamino-1,6'''-dihydroxyneomycin B or a pharmaceutically acceptable acid addition salt thereof.

6. 1-Deamino-1-hydroxyribostamycin or a pharmaceutically acceptable acid addition salt thereof.

7. A method of treating a bacterial infection in a mammal in need of same which comprises administering to said mammal an antibacterially effective amount of 1-deamino-1-hydroxyneomycin B or a pharmaceutically acceptable acid addition salt thereof.

8. An antibacterial composition comprising an antibacterially effective amount of 1-deamino-1-hydroxyneomycin B, or a pharmaceutically acceptable acid addition salt thereof, and a pharmaceutically acceptable carrier.

* * * * *